Figure 1:
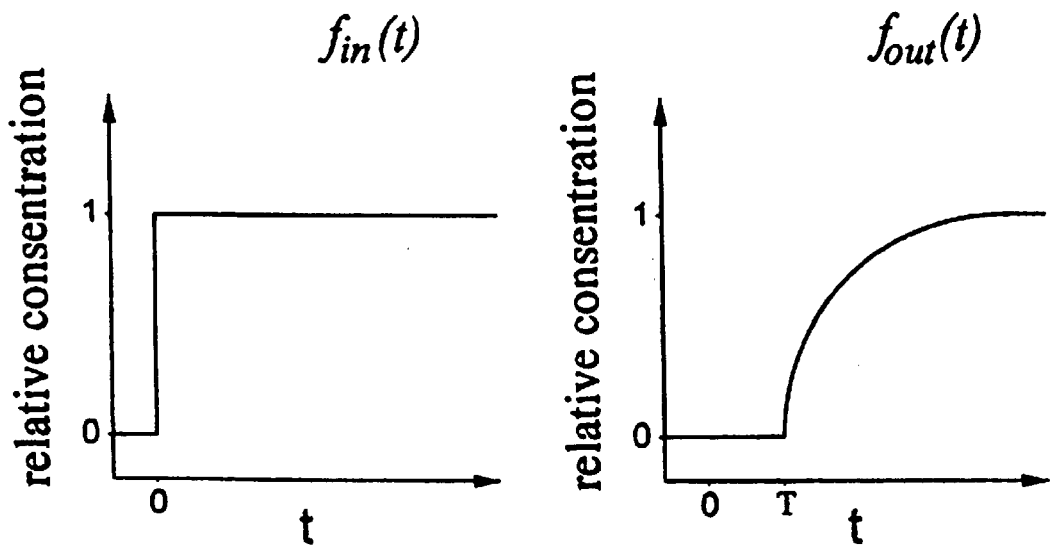

United States Patent
Silenius et al.

[11] Patent Number: 5,913,235
[45] Date of Patent: Jun. 15, 1999

[54] PROCEDURE FOR DETERMINING THE DIFFUSION COEFFICIENT PREVAILING IN A FIBRE WALL

[76] Inventors: Petri Silenius, Pallotie 5 B 10, Kirkniemi, Finland, 08800; Matti Lindström, Kuusimäenkatu 1 A, Lappeenranta, Finland, 53810; Philip Luner, 304 Demog Dr., Syracuse, N.Y. 13214

[21] Appl. No.: 08/848,582

[22] Filed: Apr. 28, 1997

[30] Foreign Application Priority Data

May 3, 1996 [FI] Finland ...................................... 961907

[51] Int. Cl.⁶ ........................... G01N 15/08; D21H 11/00
[52] U.S. Cl. ............................................. 73/38; 162/181.2
[58] Field of Search .............................. 73/38, 73, 53.03, 73/53.04; 162/181.2, 181.3

[56] References Cited

U.S. PATENT DOCUMENTS

| | | | |
|---|---|---|---|
| 4,895,019 | 1/1990 | Lehmikanagas et al. ............. | 73/53.03 |
| 5,127,994 | 7/1992 | Johansson ............................. | 162/168.3 |
| 5,601,921 | 2/1997 | Eriksson ................................ | 428/389 |

FOREIGN PATENT DOCUMENTS 0703451  3/1996  European Pat. Off. ..

OTHER PUBLICATIONS

Wochenblatt 1:1996; E.Gruber et al: Wechselwirkungen von Synthetischen Kationischen Polymeren mit Fasern und Fullstoffen, pp. 4–11.
Wochenblatt 1:1991; H.Elstner et al: Anderung der Faserstruktur Beim Receylcing . . . , pp. 5–7.
N.–E. Virkola: Puumassan Valmistus, Turku 1983, p. 685.
INSKO presentation 150–90 IV; Jan. Erik Levlin, MA: Uusiomassan Paperitekniset Ominasisuudet, p. 4.
Eero Tommila: Fysikaalinen Kemia, Helsinki 1961, p. 207, paragraphs 3 and 4.
Tappi Journal; Tom Lindstrom and Lars Wagberg, Effects of PH and Electrolyte Concentration on the Adsorption of Cationic Polyacrylamides on Cellulose, Jun. 1983, pp. 83–85.

*Primary Examiner*—Hezron Williams
*Assistant Examiner*—Jay L. Politzer
*Attorney, Agent, or Firm*—Merchant, Gould, Smith, Edell, Welter & Schmidt, P.A.

[57] ABSTRACT

The invention relates to a procedure for determining a quantity dependent on the rate of diffusion in the fibre wall for diffusion occurring through it, in which procedure a diffusible tracer is introduced into the fibres under measurement, the fibres are suspended in an aqueous phase and the tracer concentration is determined after a certain time has elapsed since the time of suspension of the fibres, and the quantity dependent on the rate of diffusion is calculated on the basis of the concentration and time.

In addition, the invention relates to a procedure for determining the proportion of secondary fibre in a fibre suspension containing primary fibre and secondary fibre, in which procedure virtual diffusion coefficients are determined in the fibre wall for diffusion taking place through it in at least two fibre suspensions for which the proportions of primary and secondary fibre are known and in a fibre suspension under measurement, and that the proportion of secondary fibre in the suspension under measurement is estimated by assuming that the diffusion coefficient depends mainly linearly on the proportion of primary and secondary fibre in the fibre suspension.

10 Claims, 2 Drawing Sheets

PROCEDURE FOR DETERMINING THE DIFFUSION COEFFICIENT PREVAILING IN A FIBRE WALL

The present invention relates to a procedure for determining a quantity dependent on the rate of diffusion in the fibre wall for diffusion occurring through it, as is defined in the preamble of claim 1. Furthermore, the invention relates to a procedure of determining the diffusion coefficient in the fibre wall in diffusion occurring through it. Further, the invention relates to a procedure for determining the proportion of secondary fibre in a fibre suspension containing primary and secondary fibre. In addition, the invention relates to a procedure for characterizing the papermaking properties of a fibre suspension.

In the present patent description, the term secondary fibre refers to fibre that has gone through the paper manufacturing process at least once. Thus, secondary fibre comprises actual recycled fibre obtained from waste paper and fibre obtained from broke produced in a paper mill. Primary fibre or virgin fibre refers to fibre that has not gone through the paper manufacturing process. Fibre refers to fibres used in paper and pulp industry, produced by chemical or mechanical methods from plants or plant parts containing lignocellulose, such as wood or plants with a herbaceous stalk, from which the lignin has been removed or in which the lignin is partly or completely preserved, such as cellulose, groundwood and/or refiner mechanical pulp or mixtures of these.

The use of secondary fibre has rapidly increased both in Europe and in the USA during the past few years, and economic prognoses predict a continuing increase. The demand for market pulp produced from recycled paper has also been growing vigorously.

Fibre recycling is controlled by various regulations and green values, but in the long run the technology will largely orient itself according to supply and demand. Naturally, a good market value of recycled paper serves as an incitement for the development of waste paper collection and sorting systems. The situation varies from one country to another. For instance, in Japan the amount of fibre recycled is very high as the country lacks natural fibre resources of its own. The Scandinavian countries have a sufficient supply of primary fibre and the amount of waste paper produced in them is relatively low as the centre of paper consumption is in Central Europe; therefore, for economic reasons alone, the use of secondary fibre has less significant proportions in Scandinavia.

Secondary fibre is treated before reuse in a so-called deinking process so as to raise its potential in paper manufacture to a level sufficient for a new paper product. The unit processes in deinking comprise both physical and chemical operations that have an effect on the fibre quality and therefore on the quality of the paper product manufactured from the secondary fibre. Also, the earlier history of the fibre in paper manufacture has an effect on the end product. The properties of paper manufactured from secondary fibre, e.g. the tensile and burst strength of the paper are worse than for paper manufactured using only primary fibre. Paper manufactured from secondary fibre generally also has a lower brightness, but this depends on the bleaching method.

When secondary fibre is used in the manufacture of a new paper product, primary fibre is almost invariably added to the pulp mixture to achieve the required product properties. Systems have been tried to develop to measure and characterize the proportion of secondary fibre and therefore the quality of the mixture, i.e. its usability.

In literature, several investigations are known which aim at characterizing secondary fibre. The aim has been to establish which fibre properties are changed in the recycling process and which ones of these changes result in a deterioration of paper properties. Mechanical operations, such as pulping and refining, are known to have an effect on the dimensions and morphology of fibres. On the other hand, the chemical deinking operations affect the surface properties of fibres, and sorting affects changes in the distribution of fibre properties. The problem is that most of the changes mentioned are too small to be reliably determined and measured. Therefore, it is difficult to establish a connection between such changes and changes in paper properties.

Some researchers (e.g. Ellis and Sedlachek) have presented justifiable arguments to the effect that the deterioration of paper strength when secondary fibre is used is due to the fact that the bond areas between secondary fibres in the fibre network of the paper are smaller than in the case of primary fibre. These statements support the idea that the deterioration in the strength properties of recycled paper is more probably due to changes in the adaptability of fibres than chemical changes in them. Adaptability means the capability of fibres to deform in the fibre network during paper manufacture so that a better contact between fibres and therefore a larger bond area are achieved.

Generally the opinion prevails that the fibre hornification occurring in recycling reduces the flexibility of fibres. Hornification occurs in paper manufacture in conjunction with the drying and it causes irreversible blocking of fibre wall micropores, thereby increasing the wall density of fibres.

For the above reasons, which have mainly arisen in connection with the use of secondary fibre, the measurement of the papermaking properties, flexibility and/or hornification of secondary fibre is of primary importance especially in view of the use of secondary fibre and in order to achieve a characterization of secondary fibre.

So far it has not been possible to determine the proportion of secondary fibre e.g. in pulp in an appropriate and satisfactory way.

The object of the present invention is to eliminate the drawbacks described above.

A specific object of the invention is to produce a new method for determining a quantity dependent on the rate of diffusion and especially determining the coefficient of diffusion from the fibre wall in diffusion occurring through the wall, which will make it possible to estimate the papermaking properties, adaptability and/or keratinization of secondary fibre in fibre mixtures.

A further object of the invention is to produce a method for estimating the proportion of secondary fibre in fibre mixtures. Yet another object of the invention is to produce a method for characterizing the papermaking properties of a fibre suspension containing secondary fibre.

As for the features characteristic of the invention, reference is made to the claims.

The invention is based on extensive investigations in which it was established that the rate of diffusion of a tracer in the keratinized wall of secondary fibre is lower than in the wall of never dried primary fibre. This is because the fibre hornification occurring in paper manufacture in conjunction with drying blocks the micropores in the fibre wall and increases the density of the wall, reducing the diffusion, the rate of diffusion and a quantity dependent on diffusion or the rate of diffusion, especially the coefficient of diffusion, in diffusion taking place through the wall.

According to the invention, a method has been developed for measuring the rate of diffusion and/or any quantity dependent on it and especially the diffusion coefficient when a tracer is being diffused through the fibre wall. The measured rate of diffusion and/or diffusion coefficient or quantities dependent on these characterize the papermaking properties or adaptability of the fibre mixture. The quantities obtained can be used to determine the proportion of hornified fibre (secondary fibre) in the fibre mixture. Moreover, the quantities obtained can be used to characterize the papermaking properties of fibre suspensions containing secondary fibre.

In the procedure of the invention, a diffusible tracer is introduced into the fibres in a fibre sample to be investigated. The fibres are then placed in water and the diffusion through the fibre wall of the diffusible tracer contained in the fibres is measured by measuring the concentration of the diffusible tracer in bulk mixture outside the fibres at a certain time or as a function of time. The total diffusion or the rate of diffusion taking place through the fibre wall can be calculated on the basis of the concentration of the bulk mixture at a given instant and/or on the basis of the change in concentration per unit of time.

For the calculation of the diffusion coefficient, the measurement data is fitted in a mathematical model describing the diffusion occurring inside the fibres, whereupon the diffusion coefficient, which describes the rate of diffusion in a known manner, and/or a quantity dependent on it can be calculated.

The tracer may be in general any water-soluble substance whose concentration can be accurately measured in a fibre suspension outside the fibres. Typical tracers are organic or inorganic acid, alkali or salt solutions ionizable or non-ionizable in the fibre suspension, neutral tracers, colorants or radiotracers. The measurement can be performed using any sufficiently fast, cheap and reliable analysing method whose dynamic behaviour is known or can be measured.

The tracer can be introduced into the fibres preferably by impregnating a fibre sample in a saturated or nearly saturated tracer solution, e.g. a salt solution, such as a halide solution of an alkaline metal. The extra tracer solution outside the fibres can be removed e.g. by pressing the fibres so that no significant amounts of tracer will remain on the outside of the fibres, or in some other way. For the measurement, the fibres thus cleaned externally are placed in a vessel provided with a vigorous mixing capability, preferably in ion-exchanged water, and the concentration of the tracer diffused in the water is determined outside the fibres as a function of time e.g. via potentiometric measurement of conductivity when the tracer is in an ionized state, or by spectrophotometry or in some other way, as is generally known in analytic chemistry.

For the determination of the rate of diffusion and diffusion coefficient, a theoretic model for the diffusion of tracer through the walls of fibres suspended in water was developed. Generally, the diffusion through the fibre wall takes place quickly and the research method applied to investigate the diffusion must be sufficiently fast to provide reliable results. Observing and measuring the diffusion in an individual fibre is difficult due to the small dimensions of the fibre. Therefore, the measurement is performed on diffusion with a known amount of fibres suspended in water. Moreover, according to the invention a new procedure was developed to allow the diffusion occurring inside the fibre to be thoroughly examined.

In developing the procedure, the starting point was a known mathematical equation for an infinite cylinder, which in practice describes a fibre of arbitrary length, in which diffusion only occurs through the fibre wall (Carslaw, H.S. et al, Conduction of Heat in Solids, $2^{nd}$ ed., Oxford University Press, Oxford (1959)).

Assuming the fibre radius to be constant, the fibre length to be much greater than the radius and the tracer concentration on the outer surface of the fibre to be zero, the radial diffusion occurring through the fibre wall can be represented according to Fick's second law in cylindric coordinates. The problem can be solved using the following initial and boundary conditions:

$$C = C_{max} \text{ when } 0 \leq r \leq R \text{ and } t = 0 \quad (1a)$$

$$C = 0 \text{ when } r = R \quad (1b)$$

$$\frac{\partial C}{\partial r} = 0 \text{ when } r = 0 \quad (1c)$$

where C is the tracer concentration inside the fibre, r is the distance from the symmetry axis of the fibre, R is the fibre radius and $C_{max}$ is the tracer concentration inside the fibre before the start of the diffusion test.

The initial condition (1a) means that the tracer must be homogeneously distributed inside the fibre before the test is started. Edge condition (1b) will be true if the suspension is effectively mixed and/or the diffusion coefficient for the tracer is much higher in water than inside the fibre wall. According to boundary condition (1c) the fibres are symmetric and undamaged.

A solution, which is a Bessel function of the first kind of order zero, can be represented as a series expansion and the constants in the solution can be determined from the initial condition (1a) (Carslaw and Jaeger, Conduction of Heat in Solids). On the other hand, as is known, the molar flow of the tracer through the fibre wall can be represented according to Fick's first law by means of the concentration gradient prevailing in the surface layer of the fibre, likewise in cylindrical coordinates. The concentration gradient can be solved by differentiating the series expansion solution of the Bessel function in the surface layer of the fibre and inserted in Fick's first law. When the molar flow occurring through the fibre wall according to Fick's first law, obtained in the manner described above, is integrated with respect to time and the result is divided by the volume of the vessel used for the measurement, the following equation is obtained:

$$C_s^* = \frac{2AC_{max}R}{V_{H_2O}} \sum_{n=1}^{\infty} \frac{1}{\beta_n^2} \left(1 - e^{-\beta_n^2 Dt/R^2}\right) \quad (2)$$

where A is the total area of the fibres, $V_{H_2O}$ is the volume of the suspension, $\beta_n$ is the n:th root of equation $J_o(\beta_n)=0$ ($J_o$ is a Bessel function of the first kind of order 0) and D is the tracer diffusion coefficient in the fibre wall.

Equation (2) gives the theoretic tracer concentration $C_s^*$ in the aqueous phase outside the fibres at different times during the diffusion test.

To obtain more accurate results, the dynamics of the measurement vessel is described as accurately as possible by means of the transfer function. For this purpose, the known method of describing the interdependence between an excitation function $f_{in}(s)$ given on the Laplace plane and a corresponding response function $f_{out}(s)$ by means of a transfer function G(s), likewise given on the Laplace plane, is used in accordance with equation (3), $$G(s) = \frac{f_{out}(s)}{f_{in}(s)} \quad (3)$$

where $f_{in}(s)$ is the Laplace transform of the theoretic concentration of the tracer in the aqueous phase, $f_{out}(s)$ is the Laplace transform of the measured concentration of the tracer in the aqueous phase and $G(s)$ is the transfer function, which describes the dynamic nature of the system as accurately as possible.

The transfer function can be determined in a separate test using no fibre in the system, by only adding concentrated electrolyte into the measurement vessel at instant t=0. In this case, $f_{in}(t)$ is a step function which has the value 1 when t>0. As for $f_{out}(t)$, it can be expressed mathematically with sufficient accuracy e.g. by equation (4), $$f_{out}(t) = 1 - e^{-(t-T)/k} \quad (4)$$

where k is a time constant and T is a time delay; k and T are parameters specific to the equipment and method of analysis and their values depend on small errors in the values at instant t=0 and on the dynamic factors relating to the mixture and the concentration measurements.

The transfer function $G(s)$ is obtained by solving the Laplace transforms for the functions $f_{in}(t)$ and $f_{out}(t)$ and inserting them in equation (3).

The final solution, corrected using the transfer function, for the measured tracer concentration outside the fibre is obtained by substituting the Laplace transform of equation (2) for the excitation function $f_{in}(s)$ and inserting the $G(s)$ thus determined in equation (3) and solving the inverse transform from the equation obtained for the response function $f_{out}(s)$ after the variable change u=t−T. For example, when function $f_{out}(t)$ is as given by equation (4), the solution obtained will be equation (5), $$\frac{C_s(u)}{C_{s(max)}(u)} = \beta \sum_{n=1}^{\infty} \frac{1}{\beta_n^2}\left[1 + \left(\frac{\gamma_n}{\frac{1}{k} - \gamma_n}\right)e^{\left(\frac{-u}{k}\right)} - \left(\frac{\frac{1}{k}}{\frac{1}{k} - \gamma_n}\right)e^{-\gamma_n u}\right] \quad (5)$$

where $C_s(u) = f_{out}(u)$ and $C_{s(max)}(u)$ is the measured tracer concentration in the plateau of the graph at the end of the test, $$B = \frac{2AC_{max}R}{V_{H_2O}} \text{ and } \gamma_n = \frac{D\beta_n^2}{R^2}.$$

The left side of equation (5) gives the relative tracer concentration.

In the procedure of the invention, to determine the diffusion coefficient prevailing in the fibre wall, in fact the average diffusion coefficient prevailing in the fibres in the fibre suspension is determined. What is obtained is therefore in the first place a apparent diffusion coefficient because the suspension consists of different kinds of fibres having different diffusion coefficients. In the procedure, it is not the different diffusion coefficients prevailing in individual fibres that are determined, but instead the procedure yields a single apparent diffusion coefficient characterizing the entire fibre suspension.

In the example measurements carried out, it was established that equation (5) describes the diffusion when ions are being diffused from inside the fibre into the surrounding water. By the aid of this equation, it is possible to solve the rates of diffusion and/or the diffusion coefficients representing the diffusion and/or quantities dependent on them. Further, the rates of diffusion and/or diffusion coefficients thus determined can be used to estimate and determine the proportion of secondary fibre in a fibre sample and/or the papermaking properties of a fibre suspension in general. The procedure of the invention is completely new and has a great importance in paper industry.

Figure 5:
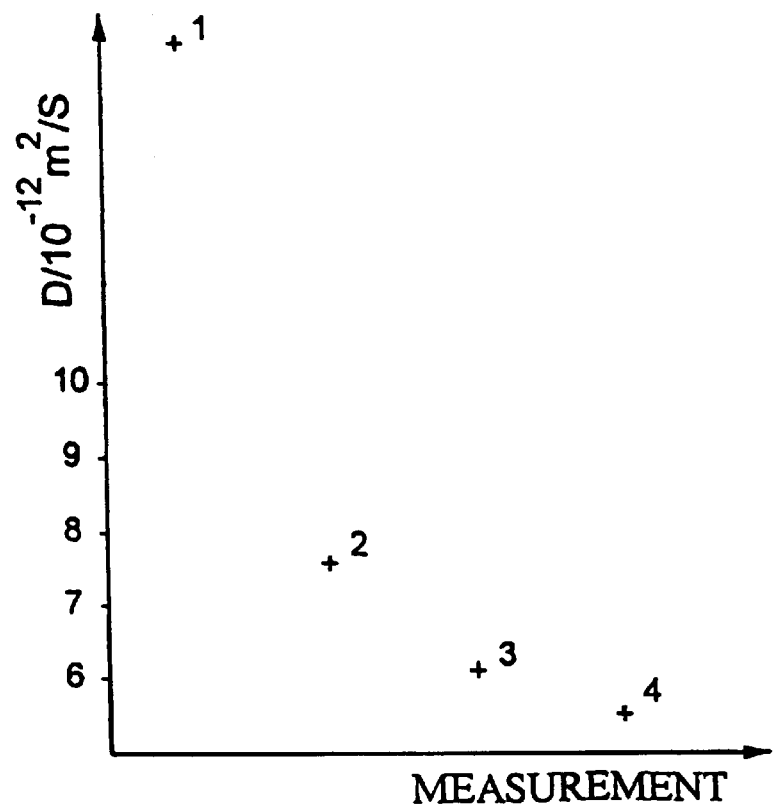
Figure 2:
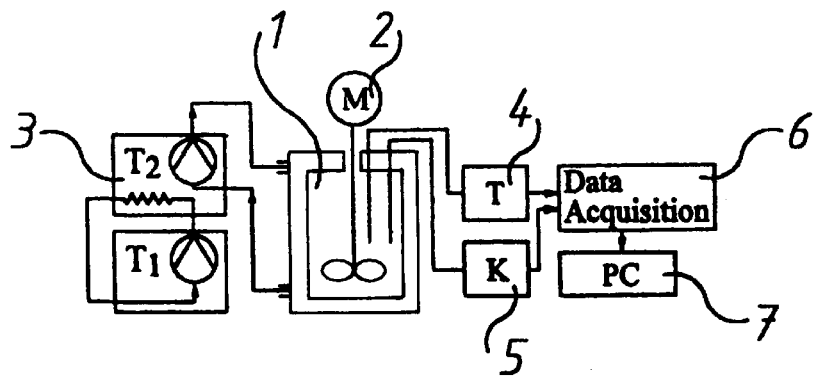
Figure 3:
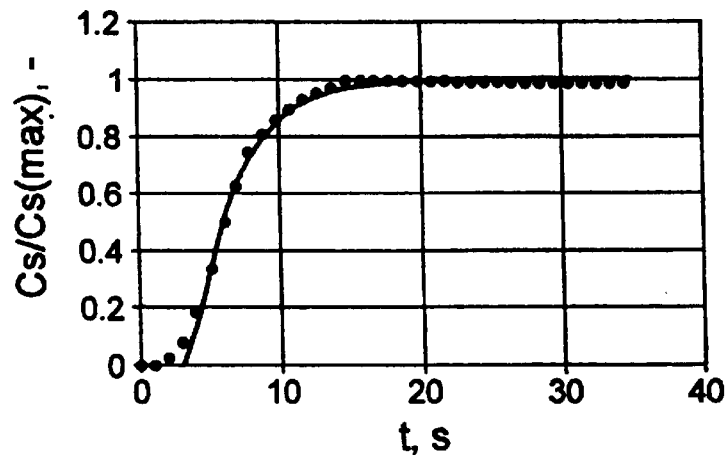
Figure 4:
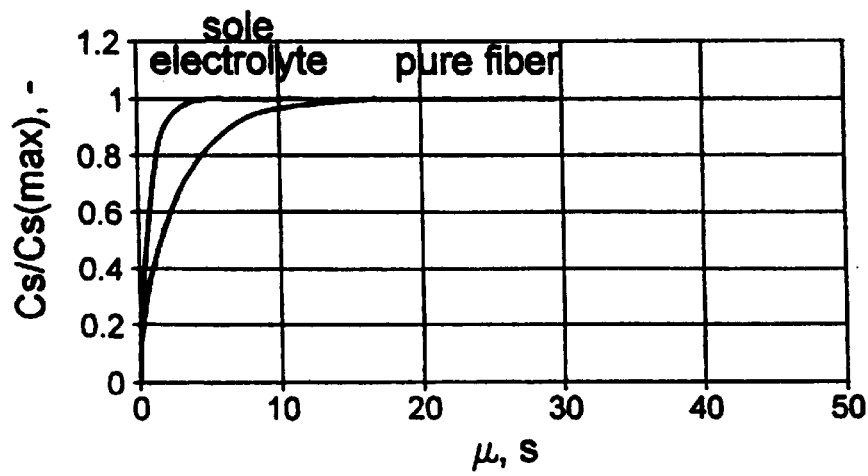

In the following, the invention is described in detail by the aid of examples of its embodiments by referring to the attached drawings, in which FIG. 1 presents a diagram representing graphs for the functions in equation (3), FIG. 2 presents a diagram representing the measuring equipment used in the examples, FIG. 3 is a graph representing the relative concentration of KCl in diffusion of KCl through the fibre wall, FIG. 4 is a graphic representation of diffusion tests, and FIG. 5 presents the diffusion coefficients determined in Example 2 as a function of the number of times the fibres have been recycled.

EXAMPLE 1

The tests were carried out using chemical birchwood pulp. Determined using laser microscope pictures and laser microscopy, the average fibre diameters were about 30 μm and 35 μm for dried fibres and for fibres suspended in water, respectively. The electrolyte used was potassium chloride (Merck, p.a.).

The equipment used in the test is shown in FIG. 2 and comprises a measurement vessel 1 provided with a mixer 2 and a temperature regulation system 3. Moreover, the equipment comprises a device 4 for measuring the temperature in the measurement vessel and a device 5 for measuring the tracer concentration in the measurement solution in the vessel, based on conductance measurement. The data were transferred to a data acquisition device 6 and further to a computer 7.

All measurements were carried out in the vessel with regulated temperature conditions, in which the temperature was 5° C. and which had a liquid volume of 500 ml; the vessel was provided with an effective mixer (mixing rate 750 1/min), and the hydrodynamic conditions were kept constant in each test.

The parameter T, the time delay and the time constant k are parameters specific to the equipment and analysing method used and they are different for different sets of equipment. The parameters can be determined separately for each case. First, to determine the time delay T and the time constant k, which are due to errors in the values of instant t=0 and the dynamic factors relating to the mixture and the concentration measurements, the conductivity of the aqueous solution, into which 3M KCl was added at instant t=0, was measured. The total amount of KCl added was the same as in tests in which fibres are used. To determine the diffusion coefficients of the electrolyte, the fibres were first impregnated with 3M KCl solution, whereupon they were pressed until there was no solution left on the outside of the fibres. At instant t=0, the fibre sample was placed in the measurement vessel and suspended by mixing at a fast rate. The increse of KCl concentration outside the fibres was monitored by measuring the conductivity of the solution as a function of time. It is generally known that concentration and conductivity are directly proportional in weak solutions. The diffusion coefficients for KCl in the fibre wall were calculated from the curve representing the dependence of the measured concentration on time, as described above.

The tests indicated that the consistency of the fibre suspension had no effect on the dynamics of the conductivity measurements and therefore on the diffusion coefficients in the range under 2 g k.a./1000 ml suspension. In the actual measurements, the amount of fibres measured was 0.25 g dry matter.

In the actual measurements the amount of fibres was so low that the electrolyte concentration on the surface of the fibres could be assumed to be zero. The final electrolyte concentration in the aqueous phase at the end of each test was not 0, but, as compared with the concentration inside the fibres at the beginning of each test, it was so low that this assumption was relatively accurate. The initial value of the time constant k was 0.79, determined from the results of conductivity measurements on a clean electrolyte by inserting the test results in equation (4).

For the calculation of the diffusion coefficients inside the fibre walls, the test results obtained in the fibre suspension measurements using the Sigma Plot curve fitting program by Jandel Scientific Co were inserted in equation (5). As a result, the values of parameters B, $D/R^2$, T and the initial level of relative concentration could be solved. The initial level of relative concentration was not assigned any value because of the small variations from the value 0. Moreover, it was impossible to accurately adjust the time delay T. Therefore, it was not attached to any value but allowed to vary freely as an adjusting parameter in each individual test. From the values of the parameter $D/R^2$, the diffusion coefficient D in the fibre wall was estimated, the average fibre radius R being known. The theoretic equation (continuous line) agreed very accurately with the test results (dotted line), as can be seen from the example in FIG. 3, which describes a typical test; the measurement results shown in FIG. 3 are also given in Table 1. The measurements on the fibres and electrolyte were repeated a few times to minimize errors. The average relative concentration curves are presented in FIG. 4.

The diffusion coefficients were calculated in the manner theoretically described above and they are presented in Table 2 together with the values of the parameters in equation (5); Table 2 shows the diffusion coefficients for KCl in the fibre wall by assuming the average radius of dry fibres to be 15 $\mu$m. The limits of error were determined at confidence level 95%.

TABLE 1

| t/s | C/C, max (measured) | C/C, max (adjusted) |
|---|---|---|
| 0 | 0 | 0.003 |
| 1 | 0 | 0.003 |
| 2 | 0.029499 | 0.003 |
| 3 | 0.073746 | 0.003 |
| 4 | 0.17699 | 0.13046 |
| 5 | 0.33333 | 0.36281 |
| 6 | 0.49263 | 0.5316 |
| 7 | 0.62832 | 0.65047 |
| 8 | 0.73156 | 0.73681 |
| 9 | 0.80826 | 0.80119 |
| 10 | 0.85841 | 0.84992 |
| 11 | 0.89381 | 0.88705 |
| 12 | 0.9233 | 0.91545 |
| 13 | 0.9469 | 0.93719 |
| 14 | 0.97345 | 0.95385 |
| 15 | 0.99705 | 0.96661 |
| 16 | 0.99705 | 0.97638 |
| 17 | 0.99705 | 0.98387 |
| 18 | 1 | 0.98962 |
| 19 | 1 | 0.99401 |
| 20 | 1 | 0.99739 |

TABLE 1-continued

| t/s | C/C, max (measured) | C/C, max (adjusted) |
|---|---|---|

After 20 seconds, the diffusion is complete.
Adjusting parameters:
initial level = 0.003
B = 4.2595 mol/m$^2$
T = 3.3385 s
D/R2 = 0.04603 1/s
D = 14.1 × 10$^{-12}$ m$^2$/s

TABLE 2

| | Diffusion coefficient Primary fibre |
|---|---|
| $D_{KCl}$, m$^2$/s | 14.6 ± 4.5 × 10$^{-12}$ |
| B, mol/m3 | 4.3 ± 0.04 |
| $D/R^2$, s$^{-1}$ | 47.8 ± 14.9 × 10$^{-3}$ |

EXAMPLE 2

In this example, the measurements were carried out in the same way as in Example 1 by recycling the fibre used in Example 1 and performing the measurements for each cycle. In measurement 1, fibre as described in Example 1 was used in the wet state; in measurement 2, the same fibre as in measurement 1, made into a sheet of paper and dried, was used; in measurement 3, the fibre used in measurement 2, made again into a sheet of paper and dried, was used; in measurement 4, the fibre used in measurement 3, made once more into a sheet of paper and dried, was used. At each stage, the fibre of the previous stage was washed very carefully before the next stage to remove the KCl.

In the measurement, the diffusion coefficients were determined. The diffusion coefficients are presented in Table 3 and in FIG. 5.

TABLE 3

| | Diffusion coefficient |
|---|---|
| Measurement 1 Undried fibre | 14.6 × 10$^{-12}$ m$^2$/s |
| Measurement 2 Fibre recycled 1 time | 7.6 × 10$^{-12}$ |
| Measurement 3 Fibre recycled 2 times | 6.1 × 10$^{-12}$ |
| Measurement 4 Fibre recycled 3 times | 5.5 × 10$^{-12}$ |

The proportion of secondary fibre in the fibre suspension under measurement can be approximately determined e.g. as illustrated by FIG. 5 by placing the measured diffusion coefficient value on the graph and reading the corresponding value defining the proportion of secondary fibre from the scale. It is to be noted that this method can only be used to define the proportion of secondary fibre as an approximate value. To obtain a more accurate result, a graph as shown in FIG. 5 can be defined more precisely by performing more measurements on known fibre suspensions, e.g. in the conditions prevailing in a given paper mill; from a more accurate graph, the proportion of secondary fibre can be interpolated more exactly. If only an approximate value of the amount of secondary fibre is desired, the proportion of secondary fibre in the fibre suspension under analysis can be estimated by assuming that the diffusion coefficient depends mainly linearly on the proportions of primary and secondary fibre in the fibre suspension. Correspondingly, the diffusion coefficient correlates with the papermaking properties of the fibre suspension, and the papermaking properties can therefore be characterized by the apparent diffusion coefficient of the fibre suspension and/or by a quantity dependent on it.

The difference between diffusion coefficients is quite clear, which means that the procedure of the invention can be used for the estimation of the proportion of secondary fibre. The greatest change occurs when the fibre is recycled for the first time, and the change becomes smaller as the number of reclaiming cycles increases. Thus, the procedure shows a more pronounced reaction to the amount of reclaimed fibre than to the number of times the fibre has been recycled. This makes it possible to estimate the proportion of recycled fibre by means of diffusion coefficients as illustrated by FIG. 5.

The proportion of secondary fibre in a fibre suspension under analysis can be estimated by assuming that the diffusion coefficient depends mainly linearly on the proportions of primary and secondary fibre in the fibre suspension. A linear scale is created using a diffusion coefficient describing non-recycled fibre, obtained from FIG. 5, and a suitably selected diffusion coefficient describing recycled fibre. A diffusion coefficient that is the most representative of recycled fibre is selected by using the diffusion coefficients representing different reclaiming cycles, e.g. as their mean value, if the suspension is likely to contain fibres differing in respect of the number of times they have been recycled. As the difference in the diffusion coefficient is small even after the first recycling cycle when the fibre is further recycled, this procedure does not involve any large error. In practice, in a given paper mill where the recycling history of the fibre is known, e.g. when estimating the proportion of fibre obtained from culled paper, the procedure can be rendered even more accurate. The curve presented in FIG. 5 can also be determined more accurately by using a larger number of measurements on known fibre suspensions in the conditions prevailing in a given paper mill.

Correspondingly, the diffusion coefficient bears a correlation to the quality of the fibre suspension, and the papermaking properties can therefore be characterized by a apparent diffusion coefficient and/or a quantity dependent on it. Although the procedure shows a more pronounced reaction to the amount of recycled fibre than to the number of times the fibre has been recycled, both have an effect of the same nature. In other words, the lower the diffusion coefficient is, the worse is the fibre mixture in respect of papermaking properties. Correspondingly, the higher the diffusion coefficient, the better is the fibre mixture in respect of papermaking properties. The model developed explains the test results very well.

EXAMPLE 3

In this example the share of secondary fibre in the fibre suspension under measurement is approximately determined as illustrated by FIG. 5 by placing the measured diffusion coefficient value on the graph and reading corresponding value defining the proportion of secondary fibre from the scale. The proportion of the secondary fibre in the suspension under analysis is estimated by assuming that the diffusion coefficient depends mainly linearly on the proportions of primary and secondary fibre in the fibre suspension. A linear scale is created using a diffusion coefficient describing non-recycled fibre, obtained from FIG. 5, and a suitably selected diffusion coefficient describing recycled fibre. A diffusion coefficient that is the most representative of recycled fibre is selected by using the diffusion coefficients representing different recycling cycles, e.g. as their mean value, if the suspension is likely to contain fibres differing in respect of the number of times they have been recycled. As the difference in the diffusion coefficient is small even after the first recycling cycle when the fibre is further recycled, this procedure does not involve any large error.

In measurement 1, primary fibre as measured in example 2 and fibre obtained from broke produced in the paper mill is used.

In measurement 2 fibre contains the primary fibre used in example 2 and recycled fibre, recycled 2, 3 and 4 times.

In measurement 1 the proportion of primary and secondary fibre is calculated assuming that the measured diffusion coefficient $9.0 \cdot 10^{-12}$ m$^2$/s depends mainly linearly on the proportion of primary and secondary fibre in the fibre suspension, i.e. the proportion of the primary fibre is $$\frac{14.6 - 9.0}{14.6 - 7.9} \cdot 100\% = 84\%$$

In measurement 2 the average diffusion coefficient of fibres recycled 2, 3 and 4 times is calculated, the result is $6.4 \cdot 10^{-12}$ m$^2$/s. The measured diffusion coefficient $9.1 \cdot 10^{-12}$ m$^2$/s is assumed to depend mainly linearly on the proportion of primary and secondary fibre in the fibre suspension, i.e. the proportion of primary fibre is:

$$\frac{14.6 - 9.1}{14.6 - 6.4} \cdot 100\% = 67\%$$

The results are presented in table 4.

TABLE 4

| Measurement | Diffusion coefficient | ΔD | Primary fibre | Secondary fibre |
|---|---|---|---|---|
| 1 | $9.0 \cdot 10^{-12}$ m$^2$/s | $6.7 \cdot 10^{-12}$ m$^2$/s | 84% | 16% |
| 2 | $6.4 \cdot 10^{-12}$ m$^2$/s | $8.2 \cdot 10^{-12}$ m$^2$/s | 67% | 33% |

According to the measurements in measurement 1 share of primary fibre was ab. 84% and secondary fibre 16% of the total amount of fibre. In measurement 2 the share of primary fibre was ab. 67% and secondary fibre (recycled 2, 3 and 4 times) ab. 33%.

The embodiment examples are intended to illustrate the invention without limiting it in any way.

We claim:

1. Procedure for characterizing the papermaking properties of a fiber suspension, including determining a virtual diffusion coefficient through the fiber wall by:

introducing a diffusible tracer into the fibers under measurement;

suspending the fibers in an aqueous phase;

determining the tracer concentration after a certain time has elapsed since the time of suspension of the fibers;

calculating the virtual diffusion coefficient on the basis of the concentration and time;

determining the virtual diffusion coefficient for a primary fiber and a secondary fiber; and comparing the virtual diffusion coefficient for the suspension with that determined for the primary fiber and the secondary fiber.

2. Procedure as defined in claim 1, wherein the tracer concentration in the aqueous phase is determined, and the diffusion coefficient is determined according to equation (2), $$C_s^* = \frac{2AC_{max}R}{V_{H_2O}} \sum_{n=1}^{\infty} \frac{1}{\beta_n^2}\left(1 - e^{1\beta_n^2 Dt/R^2}\right) \quad (2)$$

where $C_s^*$ is the electrolyte concentration outside the fibers in the aqueous phase, A is the total area of the fibers, $C_{max}$ is the initial electrolyte concentration inside the fibers, R is the fiber radius, $V_{H2O}$ is the suspension volume, $\beta_n$ is the n:th root (which is a Bessel function of the first kind of order 0) of equation $J_o(\beta_n)=0$, D is the tracer diffusion coefficient inside the fiber wall and t is time.

3. Procedure as defined in claim 2, wherein the diffusion coefficient is determined according to equation (5), $$\frac{C_s(u)}{C_{s(max)}(u)} = B\sum_{n=1}^{\infty} \frac{1}{\beta_n^2}\left[1 + \left(\frac{\gamma_n}{\frac{1}{k}-\gamma_n}\right)e^{\left(\frac{-u}{k}\right)} - \left(\frac{\frac{1}{k}}{\frac{1}{k}-\gamma_n}\right)e^{-\gamma_n u}\right] \quad (5)$$

where $C_s(u)$ is the tracer concentration measured from the aqueous phase, $C_{s\,(max)}(u)$ is the final tracer concentration in the aqueous phase, B equals $2AC_{max}R/V_{H2O}$, $\gamma_n$ equals $D\beta_n^2/R_2$, u equals t–T (where T is the length of a delay) and k is a time constant.

4. Procedure as defined in claim 1, further including the step of determining a proportion of secondary fiber in a fiber suspension containing primary fiber and secondary fiber by:
determining virtual diffusion coefficients in the fiber wall in diffusion taking place through it in at least two fiber suspensions for which the proportions of primary and secondary fiber are known and in a fiber suspension under measurement; and
estimating the proportion of secondary fiber in the suspension under measurement by assuming that the virtual diffusion coefficient depends mainly linearly on the proportion of primary and secondary fiber in the fiber suspension.

5. A method for determining the diffusion coefficient in the fiber wall in diffusion occurring through it, including:
introducing a diffusible tracer into the fibers under measurement;
suspending the fibers in an aqueous phase;
determining the tracer concentration in the aqueous phase; and
determining the diffusion coefficient according to equation (2), $$C_s^* = \frac{2AC_{max}R}{V_{H_2O}} \sum_{n=1}^{\infty} \frac{1}{\beta_n^2}\left(1 - e^{-\beta_n^2 Dt/R^2}\right) \quad (2)$$

where $C_s^*$ is the electrolyte concentration outside the fibers in the aqueous phase, A is the total area of the fibers, $C_{max}$ is the initial electrolyte concentration inside the fibers, R is the fiber radius, $V_{H2O}$ is the suspension volume, $\beta_n$ is the n:th root (which is a Bessel function of the first kind of order 0) of equation $J_o(\beta_n)=0$, D is the tracer diffusion coefficient inside the fiber wall and t is time.

6. Procedure as defined in claim 5, wherein the diffusion coefficient is determined according to equation (5), $$\frac{C_s(u)}{C_{s(max)}(u)} = B\sum_{n=1}^{\infty} \frac{1}{\beta_n^2}\left[1 + \left(\frac{\gamma_n}{\frac{1}{k}-\gamma_n}\right)e^{\left(\frac{-u}{k}\right)} - \left(\frac{\frac{1}{k}}{\frac{1}{k}-\gamma_n}\right)e^{-\gamma_n u}\right] \quad (5)$$

where $C_s(u)$ is the tracer concentration measured from the aqueous phase, $C_{s(max)}(u)$ is the final tracer concentration in the aqueous phase, B equals $2AC_{max}R/V_{H2}$, $\gamma_n$ equals $D\beta_n^2/R_2$, u equals t–T (where T is the length of a delay) and k is a time constant.

7. Procedure as defined in claim 5, wherein the tracer is introduced into the fiber by suspending the fibers in a tracer solution and removing the tracer externally from the surface of the fibers.

8. Procedure as defined in claim 5, further including the step of pressing the fibers so as to remove any tracer solution from the surface of the fibers.

9. Procedure as defined in claim 5, wherein the tracer is an electrolyte.

10. Procedure as defined in claim 5, further including the step of measuring the tracer concentration in the aqueous phase via a conductivity measurement.

* * * * *